United States Patent
Cho et al.

(10) Patent No.: US 10,213,396 B2
(45) Date of Patent: Feb. 26, 2019

(54) PATCH TO ENHANCE LOCALLY FAT METABOLISM, USING THERMOPLASTIC ELASTOMER GEL COMPOSITION INCLUDING CAPSAICIN

(71) Applicant: Senny Studio Co., Ltd., Gimpo-si (KR)

(72) Inventors: Kyu-Hak Cho, Gimpo-si (KR); Seung-Wook Yoon, Seoul (KR)

(73) Assignee: SENNY STUDIO CO., LTD., Gimpo-si (KR)

( * ) Notice: Subject to any disclaimer, the term of this patent is extended or adjusted under 35 U.S.C. 154(b) by 0 days.

(21) Appl. No.: 15/648,498

(22) Filed: Jul. 13, 2017

(65) Prior Publication Data
US 2019/0015359 A1    Jan. 17, 2019

(51) Int. Cl.
*A61K 9/70* (2006.01)
*A61K 31/165* (2006.01)
*A61K 47/06* (2006.01)
*A61K 9/00* (2006.01)

(52) U.S. Cl.
CPC .......... *A61K 31/165* (2013.01); *A61K 9/0014* (2013.01); *A61K 9/7053* (2013.01); *A61K 47/06* (2013.01)

(58) Field of Classification Search
CPC ...... A61K 9/70; A61K 9/7007; A61K 9/7015; A61K 9/7023; A61K 9/703; A61K 9/7053; A61K 9/7038
See application file for complete search history.

(56) References Cited

U.S. PATENT DOCUMENTS

| | | | |
|---|---|---|---|
| 6,197,845 B1 * | 3/2001 | Janssen | C09J 153/00 523/111 |
| 2009/0098173 A1 * | 4/2009 | Robinson | A61K 8/02 424/402 |

FOREIGN PATENT DOCUMENTS

| | | |
|---|---|---|
| KR | 10-1004329 B | 12/2010 |
| KR | 10-2015-0006765 A | 2/2014 |
| KR | 10-1417952 B | 7/2014 |
| KR | 10-2016-0122332 A | 4/2015 |

\* cited by examiner

*Primary Examiner* — Micah Paul Young
(74) *Attorney, Agent, or Firm* — Mark M. Friedman

(57) ABSTRACT

There is provided a patch to enhance locally fat metabolism, using a thermoplastic elastomer gel composition including capsaicin, which is applied to the skin surface, comprises: a skin adhering layer formed of the thermoplastic elastomer (TPE) gel including capsaicin, the skin adhering layer having a top surface and a bottom surface; a base layer secured to the bottom surface of the skin adhering layer, to support for the patch; and a removable paper/film layer secured to the top surface of the skin adhering layer, to protect the skin adhering layer prior to use, wherein the skin adhering layer comprises: 3~12 wt % of styrene ethylene butylene styrene (SEBS) or styrene ethylene ethylene propylene styrene (SEEPS), 44~53 wt % of an adhesive agent; 44~53 wt % of mineral oil, and 0.001~0.009 wt % of capsaicin. Capsaicin included in the TPE gel derives heat generation and fat breakdown, to help attain fat loss in the area where the patch is applied.

5 Claims, 2 Drawing Sheets

PATCH TO ENHANCE LOCALLY FAT METABOLISM, USING THERMOPLASTIC ELASTOMER GEL COMPOSITION INCLUDING CAPSAICIN

BACKGROUND OF THE INVENTION

1. Field of the Invention

The present invention relates to a patch to enhance locally fat metabolism and more particularly, to a patch to enhance locally fat metabolism, using a thermoplastic elastomer gel composition including capsaicin which is added to a thermoplastic elastomer gel forming a skin adhering layer to be applied to a specific area of a body, to generate heat and break down fat to help attain fat loss in the applied area.

2. Description of the Related Art

Peppers are used as a diet food since they are well-known to increase metabolism and help blood circulation and fat breakdown. It is also widely known that these effects of peppers are mainly caused by the action of the ingredient, capsaicin. As capsaicin has the features of causing burning sensation and relieving a pain, its use has been expanded to a pain reliever, pas, sports cream, etc. Meanwhile, the research result that the burning sensation is not only a feeling but also causes heat generation with fat breakdown has been published one after another.

When capsaicin is taken orally or applied to the skin, it derives heat generation by stimulating a receptor called Transient Receptor Potential Vanilloid 1 (TRPV1) which is distributed in the tongue and skin. During this process, it burns brown fat and beige fat. When capsaicin stimulates TRPV1, this signal is transmitted through sympathetic nerves, to stimulate beta-adrenaline to activate Uncoupled Protein 1 (UCP1) brown fatty tissue and beige fatty tissue, to derive the heat generation. That is, only thermal energy is generated without generating kinetic energy and during this process, fat breakdown and fat burning occur.

As food culture has been westernized due to the improvement of living standard resulting from economic development, the number of overweight people has rapidly increased and accordingly lipolysis injection procedure has been widely performed. To reduce subcutaneous fat, a process for injecting aminophylline or isoproterenol has been performed as lipolysis injection since such an ingredient has the property of deriving fat breakdown by stimulating a beta-adrenaline receptor at a topical area where the ingredient, which is originally an asthma medicine, is injected. However, this injection has a problem in that an allergic reaction or adverse reaction, such as a bruise, itch, heat sensation, seizure, etc., may occur during the injection process and it is expensive.

Currently many antiobestic drugs have been sold. Korean Published Applications Nos. 2002-20305 and 2005-81984 suggest apples, yogurt, grapes, malts, germinated brown rice, beans, fermented bean paste (Cheonggukjang), etc. as diet foods for meal replacement, to control and prevent obesity. Many people, especially, women, are greatly interested in diet. Diet foods have been sold in many different forms of an oral medicine, drink, food, cream, etc. Although capsaicin and caffeine are well-known as fat breakdown materials, oral absorption may be inactivated since the active ingredients are degraded or metabolized in the liver or stomach or an excessive intake may cause an adverse a side effect. A method of applying a cream or gel lowers the continuity of the effect.

Recently, a patch-type product which is directly applied to and adheres to the skin has been rapidly developed. A patch-type product technology is disclosed in Korean Patent No. 1417952 entitled "Patch to enhance locally fat metabolism, using skin temperature-sensitive hydrogel and process for preparing the same", in which one surface of a non-woven fabric is secured to one surface of a polyurethane film by using a glue and hydrogel is applied to the other surface of the non-woven fabric. However, this conventional art has problems in that:

First, hydrogel is a product which contains a lot of moisture by using purified water. Therefore, after opening the product, since moisture evaporates in the air, the product loses function and it has an effect only for a short time. In other words, the product cannot release the active ingredient continuously over a certain time or longer. Further, each product need to be in sealed packaging to prevent the evaporation of moisture. Furthermore, since the surface opposing to that of the non-woven fabric which is adhered to the skin is applied with polyurethane or glued with a film to prevent the evaporation of moisture, this unnecessary structure is not economical.

Second, since the active ingredient needs to be absorbed within a short time, the product has to include other ingredients, such as absorbefacient, that are not directly related to the active ingredient. In other words, the ingredient, such as sodium hydroxide, needs to be added for the solation of gel, and the ingredients, such as butylene glycol or disodium EDTA, need to be added for enhancing the absorption into the skin.

Third, the product embeds the demerit that since a lot of moisture is absorbed in hydrogel, when the moisture evaporates, it is difficult to get the desired effect. In this regard, the product may be appropriate for a mask pack or cosmetics to be used for a short time for beauty treatment but it is not proper for a patch to enhance locally fat metabolism, which is to be worn for a long time (more than several hours) or to be tightly secured to the skin area which moves a lot.

Fourth, since the adhesion of hydrogel is weak, when a user applying the patch exercises or moves a lot, the patch falls off. If an adhesive element is further added to ensure strong adhesion, it is hard to peel off the patch from the skin, causing pain and skin problems on the area applied with the patch.

SUMMARY OF THE INVENTION

Therefore, it is an object of the present invention to solve the above problems and to provide a patch to enhance locally fat metabolism, using a thermoplastic elastomer gel composition including capsaicin, to release an active ingredient, which is in a gel state at room temperature, continuously for a predetermined time (8 hours or more) reacting to skin temperature, upon being applied to the skin, by using a thermoplastic elastomer (TPE), to help attain fat loss in the applied area by using capsaicin to derive heat generation and fat breakdown, to provide a strong adhesion of the patch without causing any skin problems.

In accordance with an embodiment of the present invention, there is provided a patch to enhance locally fat metabolism, using a thermoplastic elastomer gel composition including capsaicin, which comprises: a skin adhering layer formed of the thermoplastic elastomer (TPE) gel including capsaicin, the skin adhering layer having a top surface and a bottom surface; a base layer secured to the bottom surface of the skin adhering layer, to support for the patch; and a removable paper/film layer secured to the top surface of the skin adhering layer, to protect the skin adhering layer prior to use, wherein the skin adhering layer comprises: 3~12 wt % of styrene ethylene butylene styrene (SEBS) or styrene ethylene ethylene propylene styrene (SEEPS), 44~53 wt % of an adhesive agent; 44~53 wt % of mineral oil, and 0.001~0.009 wt % of capsaicin.

Further, the thickness of the skin adhering layer is 20~400 μm, the base layer is a non-woven fabric or polyester and the thermoplastic elastomer gel is impregnated in the base layer.

Further, the mineral oil is liquid paraffin with kinematic viscosity of 60 cSt or more and the adhesive agent is a C5- or C9-based hydrocarbon resin.

Advantageous Effects of the Invention

In the patch to enhance locally fat metabolism according to the present invention, the ingredient, capsaicin, added to the thermoplastic elastomer (TPE) gel stimulates a receptor called Transient Receptor Potential Vanilloid 1 (TRPV1) of the skin tissue and thus activates a beta-adrenaline receptor, to enhance heat generation and fat breakdown simultaneously. Therefore, even though a user does not do any special exercise, the patch functions as a healthy patch to increase a body temperature, to help metabolism, blood circulation and biological activity. Specially, when the user applies the patch to a lower abdomen area, the temperature of the lower abdomen area rises to result in obtaining the subsidiary effects of large intestine movement improvement and menstrual irregularity relief, etc.

Further, in the patch according to the present invention, the mineral oil contained in the TPE gel does not evaporate at room temperature. Therefore, after opening the patch, even if the patch package is not sealed with the passage of time, the active ingredient of the functional material remains active to keep the moist feeling of the gel and provide comfortable and pleasant wearable sensation. The adhesion is strong and it is easy to peel off the patch from the skin, without hurting. Since no remnant is left on the area where the patch is applied to, it is possible to use the patch repeatedly and it is easy to change the area to be applied with the patch, without causing any skin problems.

Further, the patch according to the present invention enables fat breakdown topically, without having low efficiency and side-effects caused when fat reducing medicines are taken orally and absorbed or those are applied to the skin. In addition, during the time the patch is applied, the effect of heat generation increases the skin temperature so that the TPE gel is tightly secured to the skin, thereby strengthening the moisturization of the skin. Consequently, since this makes better conditions for the active ingredients including capsaicin to permeate into the skin, there is no need to add auxiliary ingredients, such as an absorption enhancer, an emulsifier, a skin sedative, and thus the patch is less irritable to the skin.

BRIEF DESCRIPTION OF THE DRAWINGS

The above and other features and advantages of the present invention will become more apparent to those of ordinary skill in the art by describing in detail the preferred embodiments thereof with reference to the attached drawings in which.

DESCRIPTION OF NUMBERS FOR CONSTITUENTS IN DRAWINGS

Figure 1:
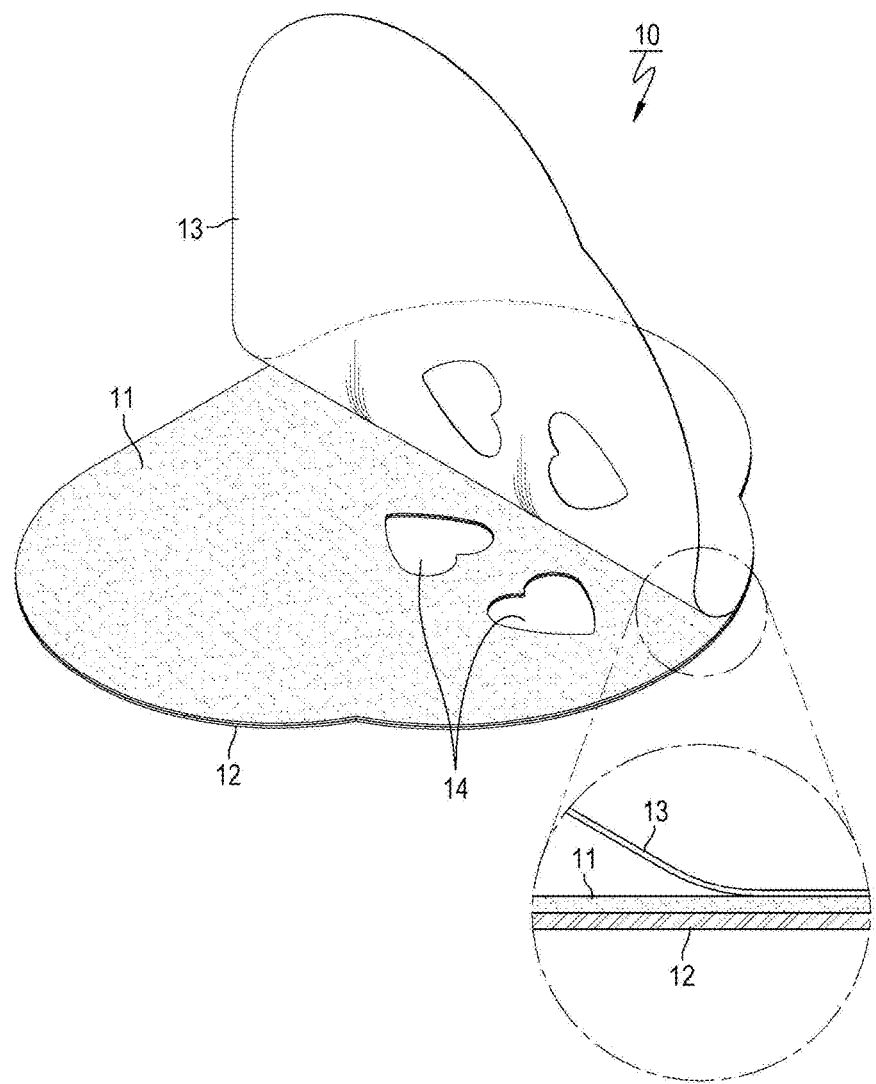
FIG. 1 is a sectional view of a patch to enhance locally fat metabolism, using a thermoplastic elastomer gel composition including capsaicin according to the present invention.

10: patch
11: skin adhering layer
12: base layer
13: removable paper/film layer
14: opening

DETAILED DESCRIPTION OF THE PREFERRED EMBODIMENT

The present invention will now be described more fully hereinafter with reference to the accompanying drawings, in which the preferred embodiment(s) of the invention is shown so that those of ordinary skill in the art can easily carry out the present invention.

The best features of a patch to enhance locally fat metabolism according to the present invention are that: the capsaicin ingredient contained in a skin adhering layer derives heat generation and fat breakdown to help attain fat loss in the area of the skin where the patch is applied; when the patch is applied to the skin, the active ingredient is rapidly released by the skin temperature so that the effect lasts for a long time (eight (8) hours or more); and since the adhesion is strong, even though a user using the patch does exercise, the patch does not fall off and it does not cause any skin problems.

In the application for the present invention, although it is described as the 'patch to enhance locally fat metabolism', the thermoplastic elastomer (TPE) gel is applied to not only those patches but also many different products to be used by being adhered to the skin, such as diapers, sanitary pads, unitary incontinence dispensers, etc. and many different purposes for use. The title of the invention and the claims recite the 'patch to enhance locally fat metabolism', however, it may be understood that the use of the thermoplastic elastomer (TPE) gel according to the present invention for the other purposes is included in the scope of the right to be protected in this application.

A patch to enhance locally fat metabolism 10 according to the present invention, which is directly attachable to or detachable from the skin in use, comprises a skin adhering layer 11 forming of thermoplastic elastomer gel (hereinafter, referred to as "TPE gel") including capsaicin and the skin adhering layer having a top surface and a bottom surface, a base layer 12 secured to the bottom surface of the skin adhering layer 11, and a removable paper/film layer 13 secured to the top surface of the skin adhering layer 11 prior to use, to be removed upon use.

The skin adhering layer 11 is formed of a composition comprising: the TPE gel comprising 3~12 wt % of styrene ethylene butylene styrene (SEBS) or styrene ethylene ethylene propylene styrene (SEEPS), 44~53 wt % of an adhesive agent and 44~53 wt % of mineral oil; and 0.001~0.009 wt % of capsaicin. The composition including the TPE gel is adhered to the skin of a human, to be rapidly absorbed into the skin and to release an ingredient continuously for a predetermined time. In the US, OTC (over-the-counter) pain control medicines or medical supplies for the temporary desensitization of nerves when capsaicin acts on transient receptor potential vanilloid 1 (TRPV1), contain capsaicin of 0.025 wt % or more. Therefore, the content of capsaicin used in the present invention is preferably 0.0025 wt % or less, to prevent the desensitization of TRPV1.

The TPE gel used in the present invention comprises a base polymer which is a block polymer, an adhesive agent and mineral oil as plasticization oil. Since the TPE gel has a glass transition temperature (−72° C.) which is similar to that of natural rubber, it has a property of soft gel and starts liquefying at a high temperature of 100° C. or higher. Thus, when it is used at room temperature, it is always moist so that the user feels good.

The block polymer as the base polymer uses styrene ethylene butylene styrene (SEBS) or styrene ethylene ethylene propylene styrene (SEEPS). Since SEBS and SEEPS are safe to a human body and has good mechanical properties, these block polymers are used as materials for medicines and cosmetics. Specifically, the typical cases using these block polymers are medicinal patches, cosmetics like a lip gloss, etc., baby diapers or personal hygiene items, etc. Since SEBS and SEEPS have better cohesiveness than the other styrene-based block polymers, these are appropriate for a patch which should not leave a remnant to the skin when removing the patch from the skin.

The adhesive agent uses a C5- or C9-based hydrocarbon resin having good compatibility with the styrene-based block polymers. Preferably, the adhesive agent may use a hydrogenated hydrocarbon resin, to secure excellent adhesion. More preferably, the adhesive agent may use a hydrogenated hydrocarbon resin among those that are allowed to be used as wraps for food or labels for food by the USA FDA or that have CAS numbers registered with the International Nomenclature of Cosmetic Ingredients (INCI).

The mineral oil as the plasticization oil uses high-purity liquid paraffin which is purified as cosmetics or additives for food. Preferably, it uses oil with kinematic viscosity of 60 cSt or more rather than low viscosity oil used for general cosmetics. Because covering/applicability, cleaning are moisturizing effect are considered as important in general cosmetics, whereas flexibility effect to the skin is more important in the TPE gel used for the patch of the present invention and the foregoing oil provides the properties of the TPE gel which is proper for the present invention. Since the mineral oil does not evaporate at room temperature, even if a time passes after manufacturing the patch product or even if the patch product is not sealed, the active ingredients remain and the moist sensation of the gel is maintained.

The dosage form prepared as described above has the property of pressure sensitive adhesives (PSA) by the structure having end-blocks at both ends of polystyrene in SEBS or SEEPS and a rubber-block at the middle thereof. Since the glass transition temperature of the PTE gel is about −72° C. which is similar to that of natural rubber, it keeps a soft gel form at room temperature and therefore when the patch is applied to the skin, it rapidly transmits the active ingredient, such as capsaicin, by reacting to the temperature of the skin.

Since the TPE gel does not contain moisture, the capability of dissolving capsaicin which is fat-soluble and transmitting capsaicin to the skin is excellent relative to a water-soluble acrylic dosage form, hydrogel dosage form or emulsion dosage form. Accordingly, it enables a continuous release (for eight hours or more) of capsaicin with a composition ratio which does not irritate the skin, and it also enables warm sensation and fat breakdown, without any side effects of skin problems or unpleasant feeling caused by the excessive content of the ingredient.

Capsaicin, which is a causative agent of a hot spice included in peppers, promotes energy metabolism inside a human body and stimulates fatty tissues, to expedite the generation of heat and burn the fatty tissues and therefore to be involved with the reduction of body fat and cholesterol. It is important to prepare the composition of capsaicin at the ratio which does not cause a stinging skin sensation. When the composition is prepared over a predetermined ratio, the user feels a stinging skin sensation and immediately removes the patch, stopping the use of the patch. In the patch of the present invention, the content of capsaicin is 0.001~0.009 wt %, however, preferably, the content of capsaicin may vary according to the areas of the body, considering that the sensitivity of capsaicin absorption is different by the areas thereof. More preferably, the content of capsaicin to be applied to the abdomen and the areas having more cellulites may be 0.003~0.008 wt % and the content capsaicin to be applied to the arms, calves, thighs, hips, etc. may be 0.001~0.003 wt %.

The patch according to the present invention is designed for eight (8) hour-use use once. This is to allow a rest period of sixteen (16) hours for skin breathing. Enabling the continuous release of capsaicin for eight (8) hours while reducing any irritants to the skin once the patch is applied is achieved by adjusting the content of capsaicin and the thickness of the skin adhering layer 11. Preferably, the thickness of the TPE gel in the skin adhering layer 11 may be 20~400 μm.

When the TPE gel is applied to the skin, it is blocked from the surrounding air, to obtain the effect of increasing the temperature and moisture of the skin. During using the patch, the effect of heat generation increases the temperature of the skin and since the TPE gel with its bottom surface attached to the non-woven fabric is tightly secured to the skin and is blocked from the surrounding air, it protects the temperature of the skin and enhances the moisturization of the skin, to make better conditions for the active materials including capsaicin to be directly absorbed into the skin. Capsaicin is diffused to be effectively absorbed into the skin, without any additional absorption enhancer or fluidization enhancer.

When a material to break down fat other than capsaicin is added in the TPE gel, an oil-soluble ingredient, such as conjugated linoleic acid (safflower seed extract) or coconut oil, is to be used but a water-soluble ingredient, such as caffeine, may be used.

One side of the base layer 12 is in contact with the TPE gel forming the skin adhering layer 11. To prevent the TPE gel from being left on the skin when removing the patch from the skin, the TPE gel and the base layer 12 have to be effectively bonded together. To this end, the TPE gel liquefied at a high temperature of 100° C. or higher needs to be diffused and penetrated into the base layer 12, so as to be impregnated at 0.01 mm or more. When the TPE gel and the base layer 12 are bonded in the aforementioned manner, since the TPE gel endures the splitting resistance when it is removed from the skin, it does not remain on the skin. Further, the material of the base layer 12 uses a non-woven fabric or polyester fabric and it does not require any devices to prevent the skin adhering layer 11 from evaporating or sliding down.

When the patch 10 is used to be applied to the lower abdomen area, it is preferable to form an opening 14 at a certain position of the patch 10 so as not to seal over the belly button. Two openings 14 may be formed to be positionable based on the body shape of the user (see FIG. 1).

EXAMPLE

Figure 2:
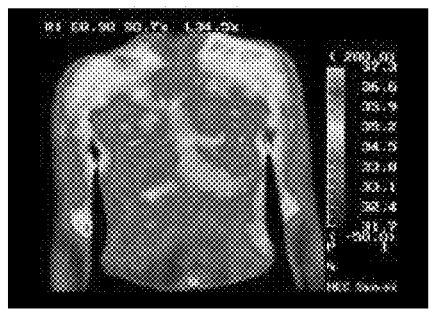
FIG. 2 is a thermal-graphic picture of a skin temperature distribution before applying the patch to the skin.
Figure 3:
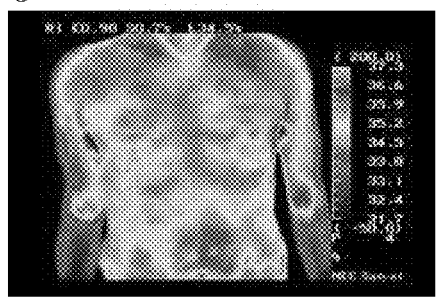
FIG. 3 is a thermal-graphic picture of the skin temperature distribution when it is two (2) hours after applying the patch to the skin.
Figure 4:
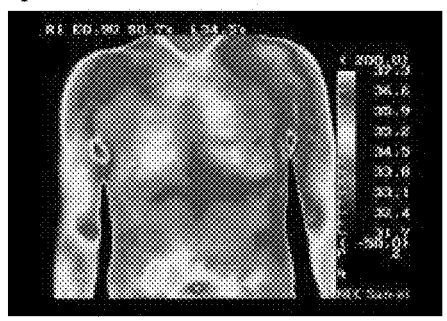
FIG. 4 is a thermal-graphic picture of the skin temperature distribution when it is two (2) hours after applying the patch to the skin.

After the TPE gel was prepared by mixing 10 wt % of the SEBS, 45 wt % of the adhesive agent and 45 wt % of the mineral oil, 0.003 wt % of capsaicin was added to the mixture, to form the skin adhering layer to manufacture the patch. After the patch was applied to the lower abdomen area of a user, the experiment to measure the temperature of the skin with the passage of a time was performed. As the result, it was confirmed that the temperature of the skin rose by 2☐, at two (2) hours (see FIG. 3) and four (4) hours (see FIG. 4), respectively, after the use of the patch, compared to before the use thereof (see FIG. 2).

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents.

Simple modifications or similar arrangements of the present invention belong to the category of the invention and therefore, the protection range of the invention will be apparent by the claims attached herewith.

What is claimed is:

1. A patch to enhance locally fat metabolism, using a thermoplastic elastomer (TPE) gel composition including capsaicin, which is applied to the skin surface, comprising:
    a skin adhering layer formed of 3~12 wt % of styrene ethylene butylene styrene (SEBS) or styrene ethylene ethylene propylene styrene (SEEPS), 44~53 wt % of an adhesive agent; 44~53 wt % of mineral oil, and 0.001~0.009 wt % of capsaicin, the skin adhering layer having a top surface and a bottom surface;
    a base layer secured to the bottom surface of the skin adhering layer, to provide support for the patch; and
    a removable paper/film layer secured to the top surface of the skin adhering layer, to protect the skin adhering layer prior to use.

2. The patch using a thermoplastic elastomer gel composition including capsaicin according to claim 1, wherein the thickness of the skin adhering layer is 20~400 μm.

3. The patch using a thermoplastic elastomer gel composition including capsaicin according to claim 1, wherein the base layer is a non-woven fabric or polyester and the thermoplastic elastomer gel is impregnated in the base layer.

4. The patch using a thermoplastic elastomer gel composition including capsaicin according to claim 1, wherein the mineral oil is liquid paraffin having kinematic viscosity of 60cSt or more.

5. The patch using a thermoplastic elastomer gel composition including capsaicin according to claim 1, wherein the adhesive agent is a C5- or C9-based hydrocarbon resin.

* * * * *